(12) United States Patent
Chang

(10) Patent No.: US 8,834,889 B2
(45) Date of Patent: Sep. 16, 2014

(54) ANTIGEN PRESENTING COMPOSITION AND USE THEREOF

(75) Inventor: Chien-Chung Chang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 385 days.

(21) Appl. No.: 13/219,963

(22) Filed: Aug. 29, 2011

(65) Prior Publication Data

US 2013/0052733 A1 Feb. 28, 2013

(51) Int. Cl.
*A61K 39/385* (2006.01)
*A61K 47/36* (2006.01)
*C07K 14/74* (2006.01)
*C12N 5/07* (2010.01)

(52) U.S. Cl.
CPC ................. C07K 14/70539 (2013.01)
USPC ....... 424/193.1; 424/278.1; 424/488

(58) Field of Classification Search
None
See application file for complete search history.

(56) References Cited

U.S. PATENT DOCUMENTS

2005/0152916 A1 * 7/2005 Cai et al. .................... 424/185.1

OTHER PUBLICATIONS

Meng et al (Biotechnol. Lett. 2009 31: 831-836).*
David N. Garboczi et al., HLA-A2-peptide complexes: Refolding and crystallization of molecules expressed in *Escherichia coli* and complexed with single antigenic peptides, Proc. Natl. Acad. Sci. USA, Apr. 1992, pp. 3429-3433, vol. 89.
Chuanlai Shen et al., Structural and functional characterization of peptide-B2m fused HLA-A2/MART127-35 complexes, Biochemical and Biophysical Research Communications, 2006, pp. 57-65, vol. 342.

* cited by examiner

*Primary Examiner* — Gerald R Ewoldt
*Assistant Examiner* — Marianne Dibrino
(74) *Attorney, Agent, or Firm* — WPAT, P.C.; Anthony King

(57) ABSTRACT

An antigen presenting composition comprising a plurality of 2-component MHC class I complexes and a carrier is described. A method for activating a group of antigen-specific CD8+ T cells comprising incubation of a group of naïve CD8+ T cells with the antigen presenting composition is also presented. A method for inducing the proliferation of a group of antigen-specific CD8+ T cells comprising incubation of a group of naïve CD8+ T cells with the antigen presenting composition is further described.

10 Claims, 10 Drawing Sheets

```
                        SEQUENCE LISTING

<160> NUMBER OF SEQ ID NOS: 15

<210> SEQ ID NO 1
<211> LENGTH: 9
<212> TYPE: PRT
<213> ORGANISM: Influenza virus
<220> FEATURE:
<221> NAME/KEY: PEPTIDE
<222> LOCATION: (1)..(9)

<400> SEQUENCE: 1

Ala Leu Ala Ile Met Val Ala Gly Leu
1               5

<210> SEQ ID NO 2
<211> LENGTH: 9
<212> TYPE: PRT
<213> ORGANISM: Influenza virus
<220> FEATURE:
<221> NAME/KEY: PEPTIDE
<222> LOCATION: (1)..(9)

<400> SEQUENCE: 2

Gly Ile Leu Gly Phe Val Phe Thr Leu
1               5

<210> SEQ ID NO 3
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 3

Lys Ile Phe Gly Ser Leu Ala Phe Leu
1               5

<210> SEQ ID NO 4
<211> LENGTH: 10
<212> TYPE: PRT
<213> ORGANISM: Human herpesvirus 4
<220> FEATURE:
<221> NAME/KEY: PEPTIDE
<222> LOCATION: (1)..(10)

<400> SEQUENCE: 4

Ser Ser Cys Ser Ser Cys Pro Leu Ser Lys
1               5                   10

<210> SEQ ID NO 5
<211> LENGTH: 66
<212> TYPE: DNA
<213> ORGANISM: Artificial Sequence
<220> FEATURE:
<223> OTHER INFORMATION: linker-b2m forward primer
<220> FEATURE:
<221> NAME/KEY: misc_feature
<222> LOCATION: (1)..(66)

<400> SEQUENCE: 5
```

```
ggaggtggtg gtggcggatc aggaggctca ggaggttcag gaggcatcca gcgtactcca        60
aagaat                                                                   66
```

<210> SEQ ID NO 6
<211> LENGTH: 56
<212> TYPE: DNA
<213> ORGANISM: Artificial Sequence
<220> FEATURE:
<223> OTHER INFORMATION: HA540-548-linker forward primer
<220> FEATURE:
<221> NAME/KEY: misc_feature
<222> LOCATION: (1)..(56)

<400> SEQUENCE: 6

```
ggcccatggc actggcaatc atggtagctg gtctaggagg tggtggtggc ggatca           56
```

<210> SEQ ID NO 7
<211> LENGTH: 56
<212> TYPE: DNA
<213> ORGANISM: Artificial Sequence
<220> FEATURE:
<223> OTHER INFORMATION: M1 58-66-linker forward primer
<220> FEATURE:
<221> NAME/KEY: misc_feature
<222> LOCATION: (1)..(56)

<400> SEQUENCE: 7

```
ggcccatggg gattttggga tttgtattca cgctcggagg tggtggtggc ggatca           56
```

<210> SEQ ID NO 8
<211> LENGTH: 57
<212> TYPE: DNA
<213> ORGANISM: Artificial Sequence
<220> FEATURE:
<223> OTHER INFORMATION: HER/neu 369-377-linker forward primer
<220> FEATURE:
<221> NAME/KEY: misc_feature
<222> LOCATION: (1)..(57)

<400> SEQUENCE: 8

```
ggccatatga agatctttgg gagcctggca tttctgggag gtggtggtgg cggatca          57
```

<210> SEQ ID NO 9
<211> LENGTH: 60
<212> TYPE: DNA
<213> ORGANISM: Artificial Sequence
<220> FEATURE:
<223> OTHER INFORMATION: LMP 340-349-linker forward primer
<220> FEATURE:
<221> NAME/KEY: misc_feature
<222> LOCATION: (1)..(60)

<400> SEQUENCE: 9

```
ggccatatgt cttcgtgctc ttcatgtcca ctgagcaagg gaggtggtgg tggcggatca       60
```

<210> SEQ ID NO 10
<211> LENGTH: 30
<212> TYPE: DNA
<213> ORGANISM: Artificial Sequence
<220> FEATURE:
<223> OTHER INFORMATION: b2m reverse primer
<220> FEATURE:
<221> NAME/KEY: misc_feature
<222> LOCATION: (1)..(30)

<400> SEQUENCE: 10

```
caactcgagc atgtctcgat cccacttaac                                        30
```

```
<210> SEQ ID NO 11
<211> LENGTH: 28
<212> TYPE: DNA
<213> ORGANISM: Artificial Sequence
<220> FEATURE:
<223> OTHER INFORMATION: HLA-A2 forward primer
<220> FEATURE:
<221> NAME/KEY: misc_feature
<222> LOCATION: (1)..(28)

<400> SEQUENCE: 11
gcgcccatgg gctctcactc catgaggt                                              28

<210> SEQ ID NO 12
<211> LENGTH: 28
<212> TYPE: DNA
<213> ORGANISM: Artificial Sequence
<220> FEATURE:
<223> OTHER INFORMATION: HLA-A2 reverse primer
<220> FEATURE:
<221> NAME/KEY: misc_feature
<222> LOCATION: (1)..(28)

<400> SEQUENCE: 12
gcgcctcgag cccatctcag ggtgaggg                                              28

<210> SEQ ID NO 13
<211> LENGTH: 27
<212> TYPE: DNA
<213> ORGANISM: Artificial Sequence
<220> FEATURE:
<223> OTHER INFORMATION: HLA-A11 forward primer
<220> FEATURE:
<221> NAME/KEY: misc_feature
<222> LOCATION: (1)..(27)

<400> SEQUENCE: 13 cggaccccccc caagacacat atgaccc                                              27

<210> SEQ ID NO 14
<211> LENGTH: 27
<212> TYPE: DNA
<213> ORGANISM: Artificial Sequence
<220> FEATURE:
<223> OTHER INFORMATION: HLA-A11 reverse primer
<220> FEATURE:
<221> NAME/KEY: misc_feature
<222> LOCATION: (1)..(27)

<400> SEQUENCE: 14
gggtcatatg tgtcttgggg gggtccg                                               27

<210> SEQ ID NO 15
<211> LENGTH: 15
<212> TYPE: PRT
<213> ORGANISM: Artificial Sequence
<220> FEATURE:
<223> OTHER INFORMATION: linker
<220> FEATURE:
<221> NAME/KEY: PEPTIDE
<222> LOCATION: (1)..(15)

<400> SEQUENCE: 15

Gly Gly Gly Gly Gly Ser Gly Gly Ser Gly Gly Ser Gly Gly Ser
1               5                   10                  15
```

ANTIGEN PRESENTING COMPOSITION AND USE THEREOF

FIELD OF THE INVENTION

The present invention relates to an antigen presenting composition, a method for activating CD8+ T cells, and a method for inducing the proliferation of CD8+ T cells.

BACKGROUND OF THE INVENTION

HLA Biology

Human leukocyte antigens (HLAs), i.e. the human major histocompatibility complex (hMHC) molecules, are encoded by a cluster of MHC genes in a continuous region on human chromosome 6 (21.31p). The major function of HLA proteins are cell-cell recognition and self-non-self discrimination in the immune system. There are two major groups of HLA, HLA class I and HLA class II. HLA class I molecules are expressed on the surface of most nucleated cells and present peptides generated mostly from an endogenous route and sometimes from an exogenous route to CD8+ T cells to stimulate their functions. The stimulated CD8+ T cells can recognize infected cells or tumor cells and kill them directly through cell cytotoxicity. Besides presenting peptides for T cell recognition, MHC class I molecules can inhibit NK cell activation by interacting with inhibitory receptors, such as KIR-2DL and KIR-3DL, on NK cell surface.

For MHC class II molecules, they can be expressed constitutively only on antigen presenting cells (APCs), such as B cells and dendritic cells, and present exogenous antigens to CD4+ helper T cells. The stimulated CD4+ T cells can either help cell-mediated immunity or help antibody production.

Generally, a fully-formed MHC class I complex has three components, a 45 kDa heavy chain, a 12 kDa $\beta_2$-microglobulin ($\beta_2$m) and an 8-10 amino acid peptide. In heavy chain, there are 3 extracellular domains (i.e., $\alpha_1$, $\alpha_2$ and $\alpha_3$), a hydrophobic transmembrane domain and a hydrophilic cytoplasmic domain. In an intact HLA class I complex, the $\alpha_1$ and $\alpha_2$ domains of heavy chain form the cleft for peptide binding and the $\alpha_3$ domain binds to $\beta_2$m and provides the species specificity for CD8 binding.

Antigen Processing Machinery (APM)

The assembly of MHC class I molecules relies on a number of chaperon proteins collectively named antigen processing machinery (APM) components in the endoplasmic reticulum (ER) lumen. The peptide presented by MHC class 1 molecules can come from the endogenous proteins produced by viruses living in the infected cells or by tumor cells. In the cytosol, these endogenous proteins are tagged with ubiquitin and cleaved into small peptides by proteasomes and/or immunoproteasomes in cells. The cleaved peptides will associate with transporters associated with antigen processing (TAP), which is an ATP-binding-cassette transporter complex composed of 70 kDa TAP1 and 74 kDa TAP2, and are transported into ER. In the ER lumen, the MHC class I heavy chain is partially folded with the chaperon protein, calnexin and BiP, initially. Subsequently, the MHC class I heavy chain will assemble with $\beta_2$m, stabilized by calreticulin and ERp57, and then connected to TAP through TAP-associated glycoprotein tapasin. Once the appropriate peptide, coming from the TAP, binds to the MHC class I molecule, calreticulin, ERp57, tapasin and TAP will dissociate from MHC class I molecule. Finally, the intact MHC class I molecule leaves the ER and is transported through endomembrane system to cell membrane for CD8+ T cell recognition.

Recombinant MHC Class I Molecules

Construction of recombinant MHC class I molecules produced by E. coli system was developed in 1992. Later, the first structure of recombinant MHC class I molecules was released. As previously mentioned, an intact MHC class I contains three components: a heavy chain, a $\beta_2$m and an 8-10 amino acid peptide. The three components are non-covalently associated. For constructing the intact MHC complex, the heavy chain and $\beta_2$m should be produced separately in the E. coli system and the small peptide needs to be synthesized artificially which is expensive, low-yielding and time-consuming.

BRIEF DESCRIPTION OF THE DRAWINGS

The invention can be more fully understood by reading the subsequent detailed descriptions and examples with references made to the accompanying drawing, wherein.

Figure 1:
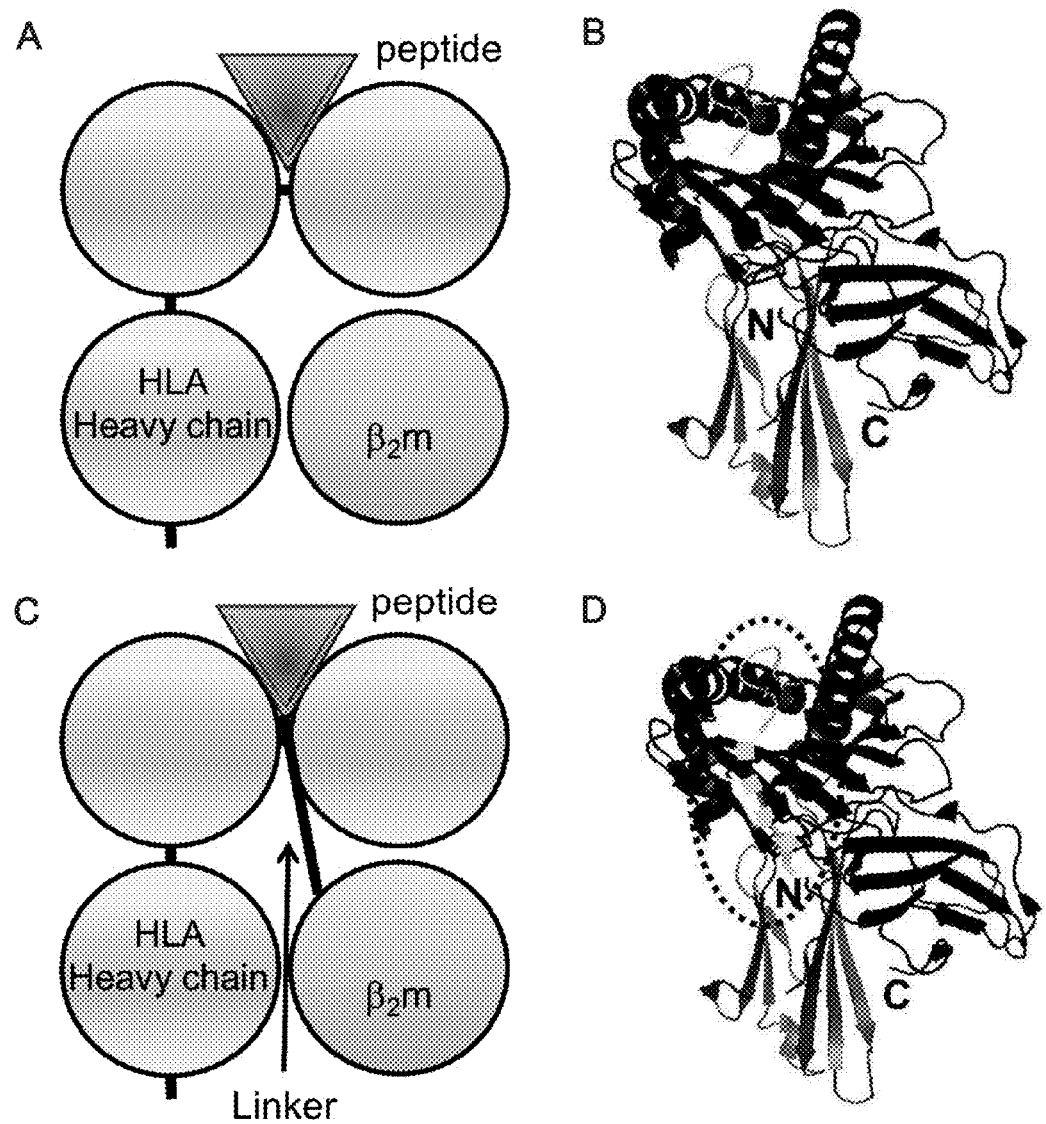
FIG. 1 shows (A and B) the 3-component (3C) construction approach and the structure of the resulting complex; and (C and D) the 2-component (2C) construction approach and the structure of the resulting complex according to one embodiment of the present invention.
Figure 2:
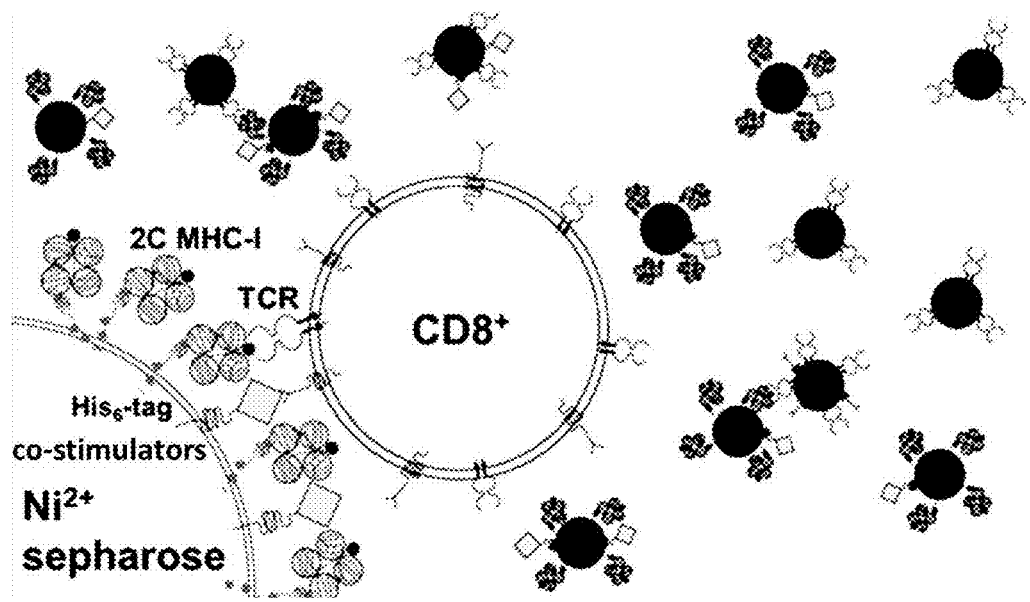
FIG. 2 shows the working model of artificial peptide presentosomes (APPs) according to one embodiment of the present invention.
Figure 3:
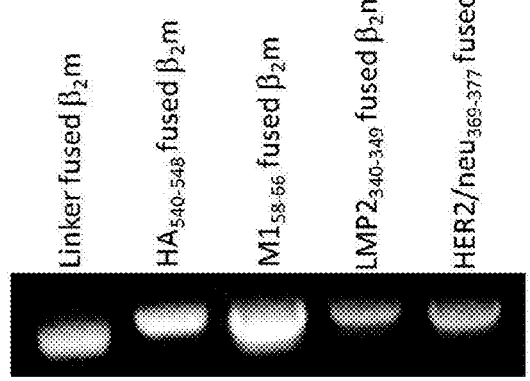
FIG. 3 shows amplification of DNA encoding (A) specific peptide linker fused-$\beta_2$m by sequential-PCR and (B) extracellular domains of HLA-A*0201 and HLA-A*1101 heavy chains by PCR according to one embodiment of the present invention.
Figure 3:

unloaded or (B) HLA-A*0201/M1$_{58-66}$-fused $\beta_2$m-loaded APPs in the presence of IL-2 and analyzed.

SUMMARY OF THE INVENTION

The present invention relates to an antigen presenting composition comprising a plurality of 2-component MHC class I complexes and a carrier; wherein the 2-component MHC class I complex comprises an α heavy chain attached to the carrier and a peptide-fused $\beta_2$m subunit. The present invention also relates to a method for activating a group of antigen-specific CD8$^+$ T cells comprising incubation of a group of naïve CD8$^+$ T cells with the antigen presenting composition. The present invention further relates to a method for inducing the proliferation of a group of antigen-specific CD8$^+$ T cells comprising incubation of a group of naïve CD8$^+$ T cells with the antigen presenting composition.

DETAILED DESCRIPTION OF THE INVENTION

Activated CD8$^+$ T cells can eliminate specifically recognized target cells. CD8$^+$ T cells recognize peptide antigens presented by MHC class I on the target cells, resulting in the destruction of the target cells by cytotoxins, such as perforin, granzyme and granulysin. Regarding the function of CD8$^+$ T cells, if a specific population of CD8$^+$ T cells can be stimulated with a specific stimulator, the stimulators can not only serve as a useful tool but also represent a potential vaccine or therapeutic platform.

Many CD8$^+$ T cell-specific stimulators have been researched and developed to date. Many of them are the whole or partial antigens administered with adjuvants, such as oil emulsions and aluminum hydroxide, to enhance the immune response. However, the effect of adjuvants should be tested case by case. In addition, the abovementioned T cell-specific stimulators are not always powerful, and the reasons require vigorous investigations to find out. Moreover, the antigens delivered by this conventional method need to go through an antigen processing and presentation process assisted by the APM components. This process is complicated and full of variables. To circumvent antigen processing and its variables, the present invention provides a platform which is easy to manipulate and can stimulate CD8$^+$ T cells more directly than the traditional strategy.

The antigen presenting composition of the present invention is useful in many aspects, such as determination of the percentage of antigen-specific CD8$^+$ T cells among peripheral blood mononuclear cells (PBMCs), stimulating antigen-specific CD8$^+$ T cells in vitro or in vivo and testing T cell receptor (TCR) affinity with the corresponding MHC class I/peptide complex.

The MHC class I complexes of the present antigen presenting composition is constructed through a 2-component (2C) construction approach. In this approach, the antigenic peptide is linked with the N-terminus of $\beta_2$m by a linker peptide which is Gly/Ser rich and flexible. This approach was investigated in 2001 for designing vaccines against the antigen presentation defective tumor cells transduced with retrovirus expressing viral peptide fused-$\beta_2$m and targeted by an antiviral immune response. It had been shown that the binding affinity to specific TCR and stimulatory ability for specific T cell response of 2C MHC class I tetramer is better than that of the 3C MHC class I complex. Therefore, for establishing a T cell-stimulating platform based on MHC class I molecules, the 2C complex may have a higher potential than the 3C complex.

To enhance the stimulatory effect, there is a need for establishing a large MHC class I polymer stimulation complex. In this disclosure, a plurality of MHC class I complex is gathered onto Ni$^{2+}$ SEPHAROSE by utilizing the His$_6$-tag fused-heavy chain. The resulting large stimulator is one kind of artificial peptide presentosome (APP).

As used herein, the term "artificial peptide presentosome" or "APP" refers to a polymer composed by a carrier and a plurality of antigen presenting complexes attached therewith. The antigen presenting complexes can be, for example but not limited to, MHC class I complex. The attachment between the carrier and antigen presenting complexes can be achieved through, for example but not limited to, the binding ability of His$_6$-tag with nickel ion. The artificial peptide presentosome can present antigen to induce activation and/or proliferation of the antigen-specific T cells with the advantage of controlling the origin of the antigen and the strength of T cell response.

As used hereinafter, the term "carrier" refers to any material that can provide a surface to which MHC class I complexes have been attached. The carrier may be a solid particle made by, for example but not limited to, metal or plastic. The examples of the carrier include, but not limited to, agarose beads, SEPHAROSE resin beads and magnetic beads.

As used hereinafter, the term "nickel ion-modified" refers to a condition in which the metal ion nickel (Ni$^{2+}$) is coated on the surface of the subject. The example of the coating method is, but not limited to, immobilizing chelating groups onto the surface of the subject, and the metal ion nickel is then coupled to the chelating matrix.

As used hereinafter, the terms "co-stimulator" refer to any molecules that can provide a co-stimulatory signal to T cells or B cells. The proliferation of lymphocytes requires both antigen binding and the receipt of a co-stimulatory signal. Co-stimulatory signals are delivered to T cells by the co-stimulatory molecules, B7.1 and B7.2, as well as related molecules that are expressed on the surface of the cell presenting antigens, through binding the T-cell surface molecule CD28. B cells may receive co-stimulatory signals from common pathogen components such as LPS, from complement fragments, or from CD40 ligand expressed on the surface of an activated antigen-specific helper T cell. The examples of the co-stimulator in the present invention include, but not limited to, recombinant B7, integrins and ICAM-1.

As used hereinafter, the terms "component" refer to elements that composed a MHC class I complex. For example, a MHC class I complex constructed by 3-component approach possesses three elements: a heavy chain, a $\beta_2$m and an 8-10 amino acid peptide. A MHC class I complex constructed by 2-component approach possesses two elements: a heavy chain and a peptide-fused $\beta_2$m.

As used herein, the term "a plurality of" is employed to describe the number of elements and components of the present invention. This description should be read to more than one unless it is obvious that it is meant otherwise.

As used herein, the term "a" or "an" is employed to describe elements and components of the invention. This is done merely for convenience and to give a general sense of the invention. This description should be read to include one or at least one and the singular also includes the plural unless it is obvious that it is meant otherwise.

As used herein, the term "or" is employed to describe "and/or".

Accordingly, the present invention provides an antigen presenting composition comprising a plurality of 2-component MHC class I complexes and a carrier; wherein the 2-component MHC class I complex comprises an α heavy chain attached to the carrier and a peptide-fused $\beta_2$m subunit.

In one embodiment, the α heavy chain is His$_6$-tagged at the C-terminus when the carrier is nickel ion-modified. In another embodiment, the carrier is made of Ni$^{2+}$ SEPHAROSE resin beads or Ni$^{2+}$ magnetic beads.

In one embodiment, the peptide-fused β$_2$m subunit comprises a peptide and a β$_2$m subunit. In another embodiment, the peptide is connected to the N-terminus of the β$_2$m subunit with a linker. In still another embodiment, the linker possesses an amino acid sequence of SEQ ID NO: 15. In another embodiment, the peptide is derived from an antigen.

In one embodiment, the antigen presenting composition further comprises a co-stimulator. In another embodiment, the co-stimulator comprises recombinant B7, integrins and ICAM-1.

The present invention also provides a method for activating a group of antigen-specific CD8$^+$ T cells comprising incubation of a group of naïve CD8$^+$ T cells with the antigen presenting composition of the present invention.

In one embodiment, the composition possesses a peptide-fused β$_2$m subunit, in which the peptide is derived from an antigen that the antigen-specific CD8$^+$ T cells are against.

The present invention further provides a method for inducing the proliferation of a group of antigen-specific CD8$^+$ T cells comprising incubation of a group of naïve CD8$^+$ T cells with the antigen presenting composition of the present invention.

In one embodiment, the composition possesses a peptide-fused β$_2$m subunit, in which the peptide is derived from an antigen that the antigen-specific CD8$^+$ T cells are against.

The next examples provide some exemplary embodiments of the present invention as follows:

EXAMPLES

The examples below are non-limiting and are merely representative of various aspects and features of the present invention.

Example 1

Selection of Specific Antigens for Constructing HLA-A*0201 and HLA-A*1101 2C Complexes The two most common HLA class I types, HLA-A*0201 and HLA-A*1101, were chosen. Each peptide antigen chosen for HLA-A*0201 and HLA-A*1101 are shown in Table 1. The peptides, namely M1$_{58-66}$, LMP2$_{340-349}$ and HER2/neu$_{369-377}$, are well-known and high-affinity peptides. Despite these well-known peptides, a bioinformatics program was also used to predict a potential peptide derived from the influenza A virus H5N1 hemagglutinin (HA). The predicted peptide sequence, HA$_{540-548}$ ALAIMVAGL (SEQ ID NO: 1), is conserved among other H5N1 strains.

TABLE 1

Specific antigens for constructing 2C MHC class I complex

| Target | Epitope | MHC class I allele | Peptide length | Peptide sequence | $IC_{50}$(nM) |
|---|---|---|---|---|---|
| Influenza virus H5N1 | $Hemmagglutinin_{540-548}$ ($HA_{540-548}$) | HLA-A*0201 | 9 | ALAIMVAGL (SEQ ID NO: 1) | 43.0 |
| Influenza virus H5N1 | Matrix protein $1_{58-56}$ ($M1_{58-65}$) | HLA-A*0201 | 9 | GILGFVFTL (SEQ ID NO: 2) | 18.8 |
| Breast Cancer | HER2/$neu_{369-377}$ | HLA-A*0201 | 9 | KIFGSLAFL (SEQ ID NO: 3) | 18.9 |
| Epstein-Barr virus | $LMP2_{340-345}$ | HLA-A*1101 | 10 | SSCSSCPLSK (SEQ ID NO: 4) | 8.2 |

Example 2

Amplification of DNA Fragments Encoding Peptide Fused-$\beta_2$m and Extracellular Domains of HLA-A*0201 and HLA-A*1101 Heavy Chains by Sequential-PCR $\beta_2$m is a 12 kDa protein encoded by 357 bp coding sequence. For generating DNA inserts which encode a flexible 15 amino-acid linker and a specific antigenic peptide attached to the N-terminus of $\beta_2$m, a set of primers was used (Table 2). The length and identity of PCR-amplified DNA fragments were checked by agarose gel electrophoresis and nucleotide sequencing. As shown in FIG. 3A, the DNA encoding linker-fused $\beta_2$m (342 bp) and each specific peptide-fused linker-$\beta_2$m (372 bp) with the right size could be obtained. For generating the DNA fragments encoding the extracellular domains of HLA-A*0201 heavy chains, a set of primers was designed as previously described. For HLA-A*1101 extracellular domains, a set of primers was designed based on the prediction by TMHMM Servers 2.0 in Expasy Proteomics Severs to determine the signal peptide cleavage site and the transmembrane domain. As shown in FIG. 3B, the DNA encoding HLA-A*0201 and HLA-A*1101 could be obtained. The nucleotide sequence of the DNA encoding peptide-fused $\beta_2$m and HLA class I heavy chains was confirmed by nucleotide sequencing analysis.

TABLE 2

Primers for amplifying peptide-linker-$\beta_2$m and HLA-A*0201 and HLA-A*1101

| Primer | Sequence (5' to 3') |
|---|---|
| linker-$\beta_2$m F (SEQ ID NO: 5) | GGAGGTGGTGGTGGCGGATCAGGAGGCTCA GGAGGTTCAGGAGGCATCCAGCGTACTCCA AAGAAT |
| $HA_{540-548}$-linker F (SEQ ID NO: 6) | GGCCCATGGCACTGGCAATCATGGTAGCTG GTCTAGGAGGTGGIGGIGGCGGATCA |
| $M1_{58-66}$-linker F (SEQ ID NO: 7) | GGCCCATGGGGATTTTGGGATTTGTATTCA CGCTCGGAGGTGGTGGTGGCGGATCA |
| HER2/$neu_{369-377}$-linker F (SEQ ID NO: 8) | GGCCATATGAAGATCTTTGGGAGCCTGGCA TTTCTGGGAGGTGGTGGTGGCGGATCA |
| $LMP2_{340-349}$-linker F (SEQ ID NO: 9) | GGCCATATGTCTTCGTGCTCTTCATGTCCA CTGAGCAAGGGAGGTGGTGGTGGCGGATCA |
| $\beta_2$m R (SEQ ID NO: 10) | CAACTCGAGCATGTCTCGATCCCACTTAAC |

TABLE 2-continued Primers for amplifying peptide-linker-$\beta_2$m and HLA-A*0201 and HLA-A*1101

| Primer | Sequence (5' to 3') |
|---|---|
| HLA-A2 F (SEQ ID NO: 11) | GCGCCCATGGGCTCTCACTCCATGAGGT |
| HLA-A2 R (SEQ ID NO: 12) | GCGCCTCGAGCCCATCTCAGGGTGAGGG |
| HLA-A11 F (SEQ ID NO: 13) | CGGACCCCCCCAAGACACATATGACCC |
| HLA-A11 R (SEQ ID NO: 14) | GGGTCATATGTGTCTTGGGGGGGTCCG |

Example 3

Production of Extracellular Domains of HLA-A*0201 and HLA-A*1101 and Peptide Fused-$\beta_2$m by the *E. Coli* System and Subsequent Purification by $Ni^{2+}$ Affinity Column Chromatography Methods:

Plasmids and *E. Coli* Strains for *E. Coli* Expression System pET28a+ and pET23a+ (Merck KGaA, Darmstadt, Germany) vectors which contain a strong bacteriophage T7 transcription promoter and a lac operator were chosen for expressing target genes in *E. coli* expression system. These vectors were propagated in the *E. coli* strain DH5α. The *E. coli* strain BL21 (DE3) was the host *E. coli* used for expressing the target genes. Both *E. coli* strains were purchased from Yeastern Biotech Co. (Taipei, Taiwan).

Production of Recombinant Proteins by the *E. Coli* System

Six constructs, i.e. pET28a+-HLA-A*0201, pET28a+-HLA-A*1101, pET28a+-HA$_{540-548}$-linker-$\beta_2$m, pET28a+-M1$_{58-66}$-linker-$\beta_2$m, pET23a+-HER2/neu$_{369-377}$-linker-$\beta_2$m and pET23a+-LMP2$_{340-349}$-linker-$\beta_2$m, were generated by PCR cloning and used individually to transform *E. coli* BL21 (DE3). Antibiotics-resistant single colonies were picked up and cultured at 37° C. After the O.D. 600 of the transformed *E. coli* BL21 (DE3) culture reached 0.3, isopropyl β-D-1-thiogalactopyranoside (IPTG) was added with a final concentration of 1 mM to induce protein expression. The expression of each protein was induced under different culturing conditions. For instance, the condition of shaking (200 rpm) at 37° C. for 8 hrs was employed to express HLA-A*0201; the condition of shaking (200 rpm) at 37° C. for 12 hrs was employed to express HLA-A*1101; and the condition of shaking (200 rpm) at 37° C. for 16 hrs was employed to express other recombinant peptide-fused $\beta_2$m protein.

Denaturation and Purification of Recombinant Proteins

The *E. coli* culture was harvested and resuspended in lysis buffer (50 mM Tris-HCl, 100 mM NaCl, 1.4 mM β-mercaptoethanol (βME), 1×EDTA free protease inhibitor cocktail set III (Calbiochem, La Jolla, Calif.)), incubated on ice for 30 mins and then homogenized by high-pressure homogenizer Emulsiflex-C5 (Avestin Inc; Ottawa, Ontario, Canada). To collect the inclusion bodies, the homogenized sample was centrifuged at 12000 rpm for 20 mins. The supernatant was removed and the inclusion body pellets were solubilized with solubilization buffer (50 mM Tris-HCl, 100 mM NaCl, 1.4 mM βME, 6M urea) in 50 ml/1 L culture at 4° C. for 2 hrs. The solubilized samples were centrifuged at 12000 rpm for 20 mins to remove the insoluble cell debris.

To purify the recombinant proteins, the solubilized samples were loaded onto the His-trap affinity column (GE Healthcare Bio-Science AB, Uppsala, Sweden) at the rate of 1 ml/min. The columns were washed with washing buffer (50 mM Tris-HCl, 100 mM NaCl, 1.4 mM βME, 6M urea, 20 mM imidazole) and eluted with the elution buffer (50 mM Tris-HCl, 100 mM NaCl, 1.4 mM βME, 6M urea, 300 mM imidazole). The elution was collected fractions by fractions (1 ml/fraction).

Coomassie Brilliant Blue R-250 Staining

The purity of resulting His$_6$-tagged recombinant proteins was checked by sodium dodecyl sulfate polyacrylamide gel electrophoresis (SDS-PAGE) (10% for recombinant heavy chain, 12% for recombinant $\beta_2$m). The loading volume of each lane was as follows: 24 µl for supernatant; 30 µl for flow through; 3 µl for washing buffer; and 2 µl for elution. The samples, which were separated by SDS-PAGE, were stained with the Coomassie brilliant blue R-250 staining buffer (3 mM coomassie brilliant blue R-250, 45% methanol, 10% glacial acetic acid) for 30 mins and then destained with destaining buffer (20% methanol, 10% glacial acetic acid).

Results:

The pET-system, which can be induced by adding IPTG in *E. coli* BL21 (DE3), was employed to produce heavy chains and peptide-fused $\beta_2$m. Proteins produced by the pET-system possess a His$_6$-tag at their C-termini.

Figure 4:
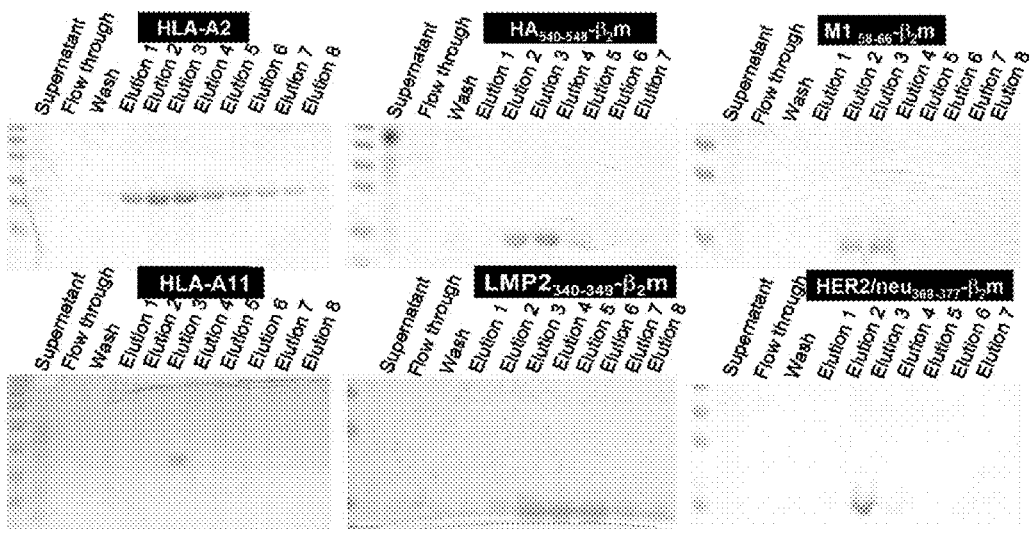
FIG. 4 shows purification results of HLA-A*0201 and HLA-A*1101 extracellular domains of heavy chain and peptide-fused $\beta_2$m by $Ni^{2+}$ affinity column chromatography according to one embodiment of the present invention.

In this case, all the recombinant proteins were localized in the inclusion bodies. The inclusion bodies were solubilized and denatured by 6M urea buffer. The denatured proteins were purified by flowing through $Ni^{2+}$ His-Trap columns. For checking the purity of recombinant proteins, samples were collected from the flow through, wash buffer and each fraction of elution. The samples were analyzed by SDS-PAGE and stained with Coomassie brilliant blue R-250 staining buffer. As shown in FIG. 4, the purification procedure could exclude unwanted proteins. Moreover, the recombinant proteins were concentrated from $2^{nd}$ to $5^{th}$ fractions.

Example 4

Analysis of the Conformation of Refolded HLA-A*0201/Peptide-fused $\beta_2$m and HLA-A*1101/Peptide-fused $\beta_2$m Complexes by Direct ELISA and Competitive-ELISA Assay Methods:

1. Refolding the 2C MHC Class I Complexes in vitro

Urea was removed from the solubilized solution of purified recombinant proteins by dialysis against PBS. The final concentration of urea was less than 0.3 nM, which was only $1/10^9$ of the original concentration. The recombinant protein (1.7 mg for heavy chain and $\beta_2$m) were injected forcefully to the 50 ml stirring refolding buffer (400 mM L-arginine, 100 mM Tris, 2 mM EDTA, 5 mM reduced L-glutathione, 0.5 mM oxidized L-glutathione, pH8.3) by a syringe as close to the stirring bar as possible at 4° C. After that, 1.7 mg heavy chain recombinant protein was further injected into the stirring refolding buffer every 14 hrs for twice. Fourteen hours after the last injection, the refolding buffer was concentrated from 50 ml to 3~4 ml. The concentrations of recombinant proteins were quantified by Bio-Rad Protein Assay (Bio-Rad, Hercules, Calif.).

2. Direct- and Competitive-ELISA Assay

For direct-ELISA, each recombinant 2C MHC class I complex was coated onto plates at increasing concentrations by utilizing coating buffer (44 mM NaHCO$_3$, 6 mM Na$_2$CO$_3$, pH9.6) at 4° C. for 14 hr. The plates were then washed twice with 0.05% Tween 20/PBS, once with PBS and were blocked with 1% BSA/PBS for 1 hr. After blocking, the plates were washed again and then incubated with 100 µl monoclonal antibody (mAb) CR11-351 (1 µg/ml) (Russo, C. et al. 1983.

Immunogenetics 18: 23) or mAb LGIII 147.4.1 (1 µg/ml) (Wang, X. et al. 2003. Tissue Antigens 62: 139) for detecting HLA-A*0201 or HLA-A*1101 complexes, respectively. After 1 hr of said incubation, the plates were washed and incubated with rabbit anti-$\beta_2$m polyclonal antibodies, FL119 (Santa Cruz Biotechnology, Inc., Santa Cruz, Calif.), at the dilution ratio of 1:1000 for 1 hr. Then, the plates were washed and incubated with horseradish peroxidase (HRP)-conjugated goat anti-rabbit antibodies (Jackson ImmunoResearch Laboratories, Inc. West Grove, Pa.) at the dilution ratio of 1:10000 for 1 hr. After said incubation, the plates were washed, added with 3,3',5,5'-Tetramethyl benzidine (TMB) substrate (Kirkegaard & Perry Laboratories, Inc., Gaithersburg, Md.) and incubated in the dark for color development. The OD value of the colors was measured at 450 nm by an ELISA reader.

For competitive-ELISA, mAb CR11-351 (2 µg/ml) was coated in each well at 4° C. for 14 hrs. The wells were washed as previously described and then incubated with recombinant proteins in different concentrations (from 0 µg to 20 µg) or 2 µg BSA as a blank control for 1 hr. Before being added to the wells, the recombinant proteins had been pre-incubated with mAb CR11-351 (1 µg) for 14 hrs at 4° C. After 1 hr of incubation, the wells were washed and then incubated with HRP-conjugated goat anti-mouse antibodies for 1 hr. The wells were washed again and then incubated with the TMB substrate in the dark for sufficient color development. The OD values were measured at 450 nm by an ELISA reader. The formula employed to calculate the inhibition percentage was as follows:

$$\text{Inhibition percentage (\%)} = \frac{0 \; \mu g \; \text{recombinant} \; OD_{450} - X \; \mu g \; \text{recombinant} \; OD_{450}}{0 \; \mu g \; \text{recombinant} \; OD_{450} - 2 \; \mu g \; BSA \, OD_{450}}$$

Results:

The purified and denatured proteins were dialyzed against PBS and refolded with oxidized- and reduced-glutathione. To determine whether the refolded MHC class I complexes have correct conformation, two kinds of ELISA assay were utilized for confirmation analysis.

Figure 5:
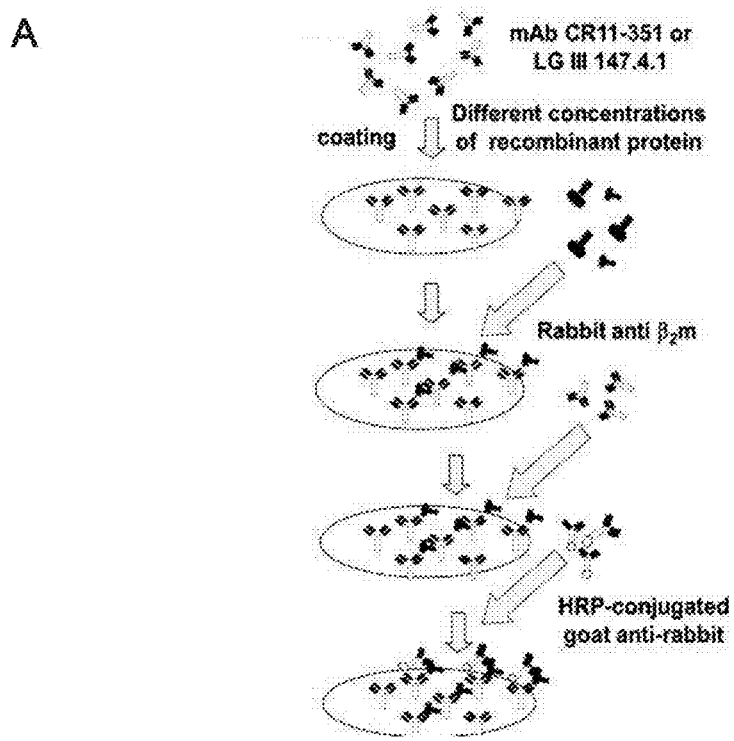
FIG. 5 shows the design (A) and results (B) of the experiments testing the conformation of refolded HLA-A*0201/peptide-fused $\beta_2$m and HLA-A*1101/peptide-fused $\beta_2$m complexes by enzyme-linked immunosorbent assay (ELISA) according to one embodiment of the present invention.
Figure 5:
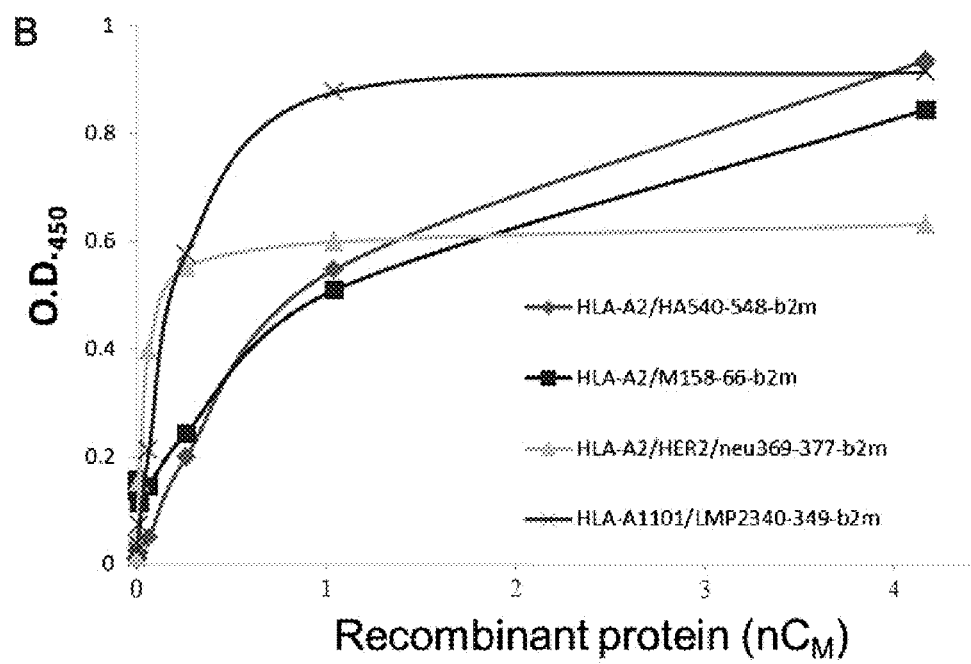

In direct-ELISA, HLA-A*0201 heavy chain conformation-specific mAb CR11-351 was used to capture intact HLA-A*0201 complexes and HLA-A conformation-specific mAb LG III 147.4.1 was used to capture intact HLA-A*1101 complexes. The intact MHC class I complexes were recognized by FL119, the rabbit anti-human $\beta_2$m polyclonal antibodies, and detected by HRP-conjugated goat anti-rabbit polyclonal antibodies. As shown in FIG. 5, the light absorbance values at 450 nm have a positive correlation with the concentration of recombinant protein. Moreover, two of the four complexes, HLA-A*0201/M1$_{58-66}$-fused $\beta_2$m and HLA-A*1101/LMP2$_{340-349}$-fused $\beta_2$m reached saturated absorbance values at 4 nC$_M$. This suggests that the two complexes can saturate the coated mAb CR11-351 or mAb LG III 147.4.1 at barely 4 nC$_M$.

Figure 6:
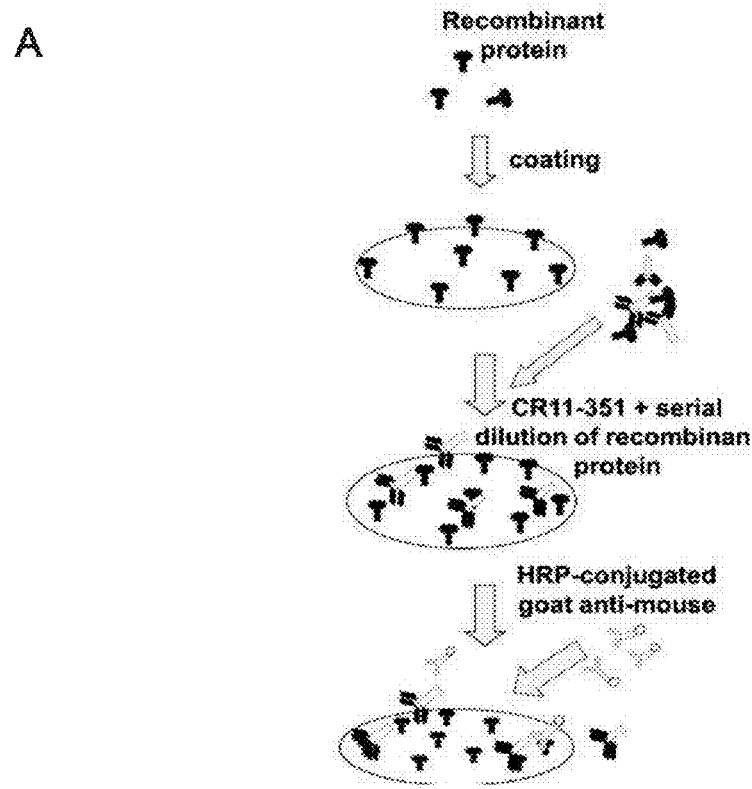
FIG. 6 shows the design (A) and results (B) of the experiments testing the conformation of refolded HLA-A*0201/peptide-fused $\beta_2$m complexes by competitive-ELISA according to one embodiment of the present invention.
Figure 6:
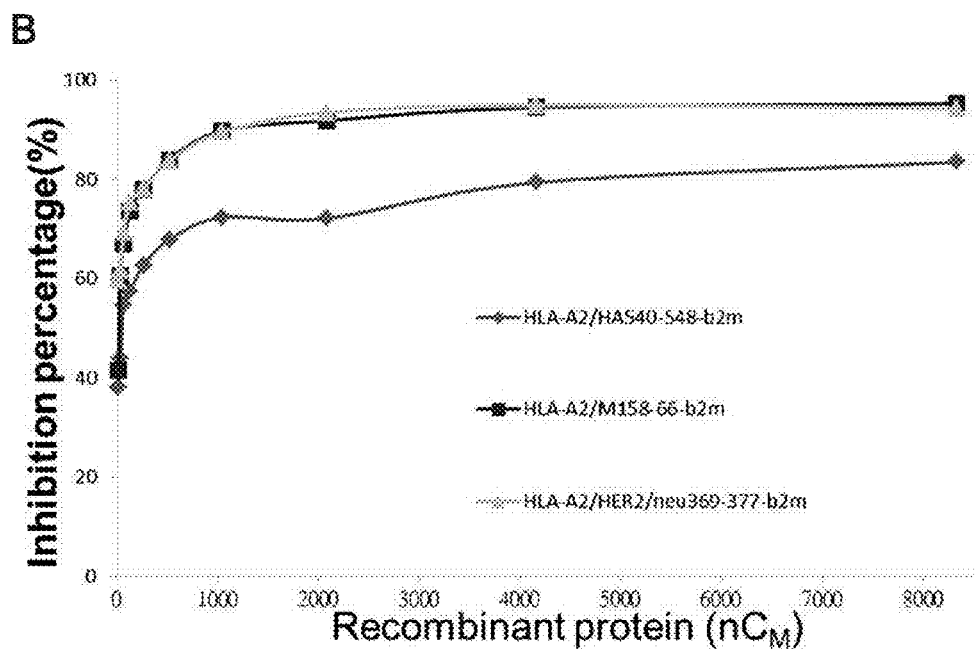

In competitive-ELISA, the mAb CR11-351 was pre-incubated with recombinant HLA*0201/peptide-fused $\beta_2$m complex protein at various concentrations in solution. Therefore, if recognition occurs, HLA*0201/peptide-fused $\beta_2$m complex-conditioned mAb CR11-351 cannot bind to the HLA*0201/peptide-fused $\beta_2$m complex proteins pre-coated on the wells. The coated recombinant HLA*0201/peptide-fused $\beta_2$m complex proteins recognized by unoccupied mAb CR11-351 were then labeled with HRP-conjugated goat anti-mouse antibodies (Jackson ImmunoResearch Laboratories, Inc.) and analyzed by TMB substrate reaction which was measured at O.D. 450. The inhibition percentage had a positive correlation with O.D. 450. As shown in FIG. 6, the inhibition percentage increased with the concentration of pre-incubated recombinant HLA*0201/peptide-fused $\beta_2$m complex proteins. The 50% inhibition concentration (IC$_{50}$) of three chosen HLA-A*0201/peptide-fused $\beta_2$m complexes, HLA-A*0201/HA$_{540-548}$-fused $\beta_2$m, HLA-A*0201/M1$_{58-66}$-fused $\beta_2$m, and HLA-A*0201/HER2/neu$_{369-377}$-fused $\beta_2$m, were 4.08 nC$_M$, 0.1 nM and 0.1 nC$_M$, respectively.

Example 5

Analysis of the Conformation of Refolded HLA-A*0201/Peptide Fused $\beta_2$m and HLA-A*1101/Peptide Fused $\beta_2$m Complexes by Immunoprecipitation (IP) Assay Methods:

1. Immunoprecipitation

The conformation of refolded MHC class I/peptide-fused $\beta_2$m complexes was analyzed by immunoprecipitation. Each refolded complex (IP-input, 40 µg), was incubated with 40 µl 50% protein A/G agarose (Thermo Fisher Scientific Inc., Waltham, Mass.), which had been washed with 1 ml PBS 3 times at 4° C. for 2 hrs, and then centrifuged at 10000 rpm for 1 min. The supernatant, which was called pre-clean lysate, was collected and was incubated with $\beta_2$m-specific mAb L368 (Lampson, L. A. et al. 1983. J. Immunol. 30: 2471) for 14 hrs by inverting the tube gently. Subsequently, the mixture was incubated with 40 µl pre-cleaned 50% protein A/G agarose for 2 hrs at 4° C. and separated into IP-bound (precipitated pellet) and IP-unbound (supernatant) by centrifugation at 5000 rpm for 2 mins. The IP-bound sample was washed by 1 ml PBS 3 times.

2. Western Blotting

The IP-bound sample and IP-input (10 µg) was dissolved in 40 µl PBS and mixed with 16 µl sample buffer (100 mM Tris-HCl, pH6.8, 5% $\beta$ME, 4% SDS, 0.2% bromophenol blue, and 20% glycerol). These samples were heated at 95° C. for 15 mins and separated by reducing SDS-PAGE. The gels, the methanol-activated polyvinylidene fluoride (PVDF) membranes (Millipore, Billerica, Mass.) and filter papers (Sartorius Stedim Biotech S.A., Goettingen, Germany) were soaked in transfer buffer (12 mM Tris-HCl, 96 mM glycine and 20% methanol) for 10 mins. The proteins were transferred from gel to PVDF membrane by Semi-Dry Electrophoretic Transfer Cell (Bio-Rad) for 45 mins.

The transferred PVDF membrane was blocked in 2% BSA and 5% dry-milk in PBS for 30 mins. After blocking, the membranes were incubated with mAb TP25.99 (10 µg/ml) (Desai, S. A, et al. 2000. J. Immunol. 165: 3275) and mAb L368 (5 µg/ml) for 14 hrs at 4° C. with gentle shaking. Next, membrane was washed with PBS containing 0.05% Tween 20/PBS and PBS sequentially, and then incubated with HRP-conjugated goat anti-mouse antibodies for 30 mins. The membrane was washed, incubated with the ECL substrate (PerkinElmer, Waltham, Mass.) and exposed to the film (GE Healthcare Biosciences, Piscataway, N.J.).

Figure 7:
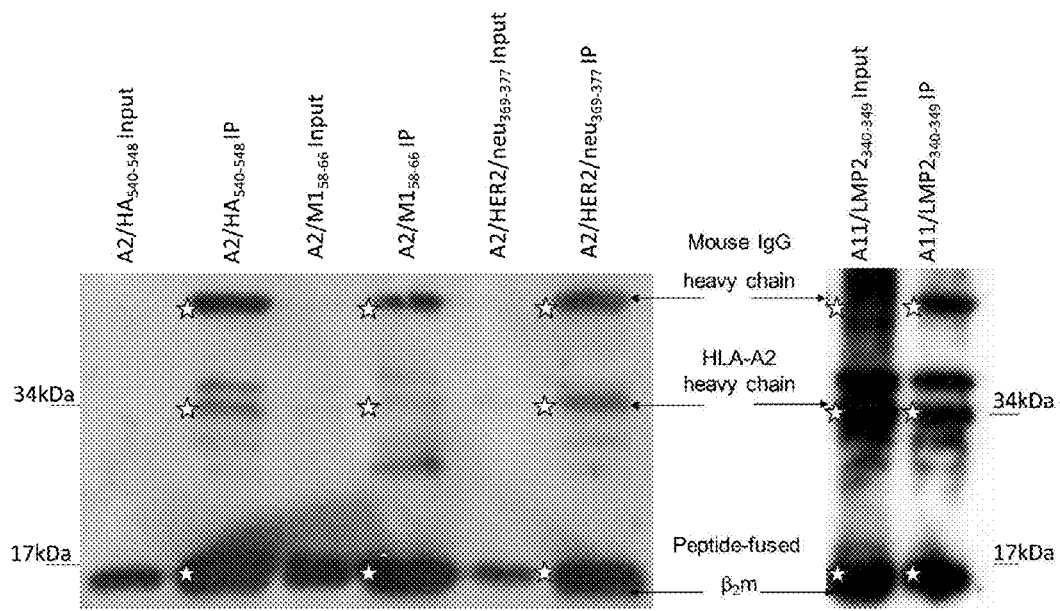
FIG. 7 shows the immunoprecipitation results of the HLA-A*1101 and HLA-A*0201 heavy chains with peptide-fused $\beta_2$m for determining the association between them according to one embodiment of the present invention.
Figure 8:
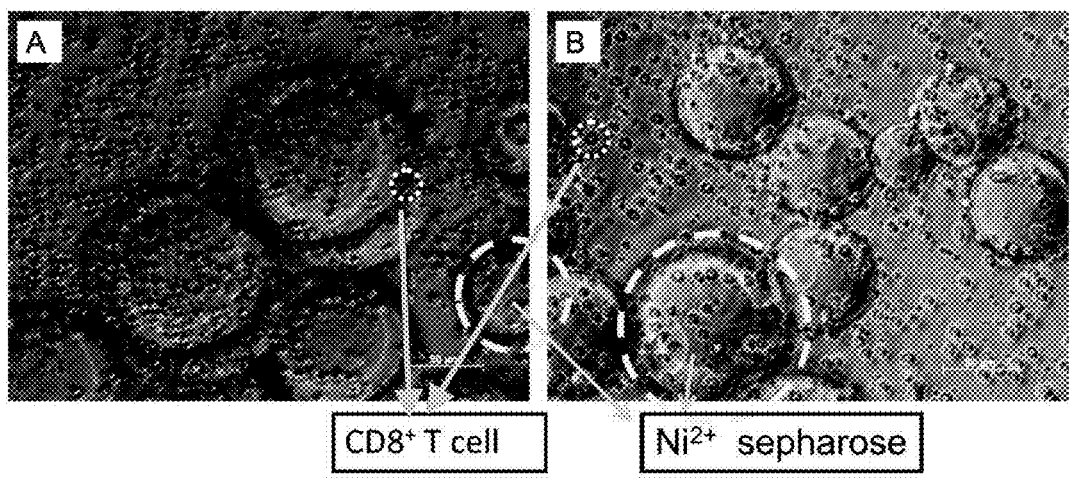
FIG. 8 shows the binding and gathering of HLA-A*0201-restricted CD8+ T cells to 2C HLA-A*0201/peptide-fused $\beta_2$m complex-loaded $Ni^{2+}$ SEPHAROSE beads (crosslinked agarose beads) according to one embodiment of the present invention. The mentioned 2C HLA-A*0201/peptide-fused $\beta_2$m complex-loaded $Ni^{2+}$ SEPHAROSE beads were co-cultured with T cells from (A) an HLA-A*0201+ individual and (B) a non-HLA-A*0201 individual.
Figure 9:
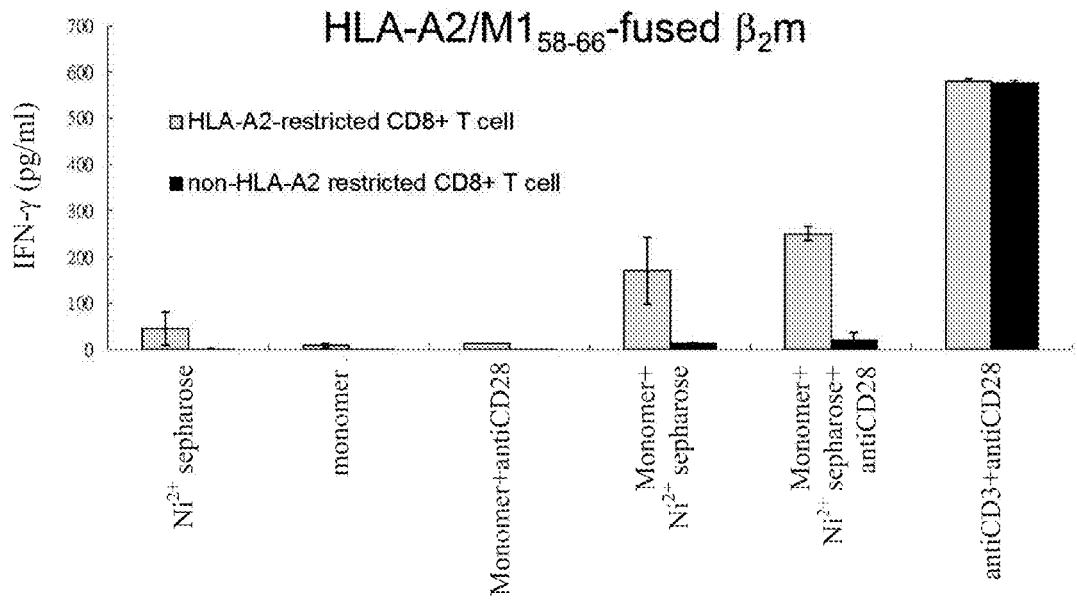
FIG. 9 shows the response of HLA-A*0201-restricted, antigen-specific T cells stimulated by HLA-A*0201/peptide-fused $\beta_2$m complex-loaded APPs according to one embodiment of the present invention. HLA-A*0201+ and non-HLA-A*0201 lymphocytes were co-cultured with (A) HLA-A*0201/M1$_{58-66}$-fused $\beta_2$m-loaded or (B) HLA-A*0201/HA$_{540-548}$-fused $\beta_2$m-loaded APPs and IFN-$\gamma$ secretion was measured. **p<0.01
Figure 9:
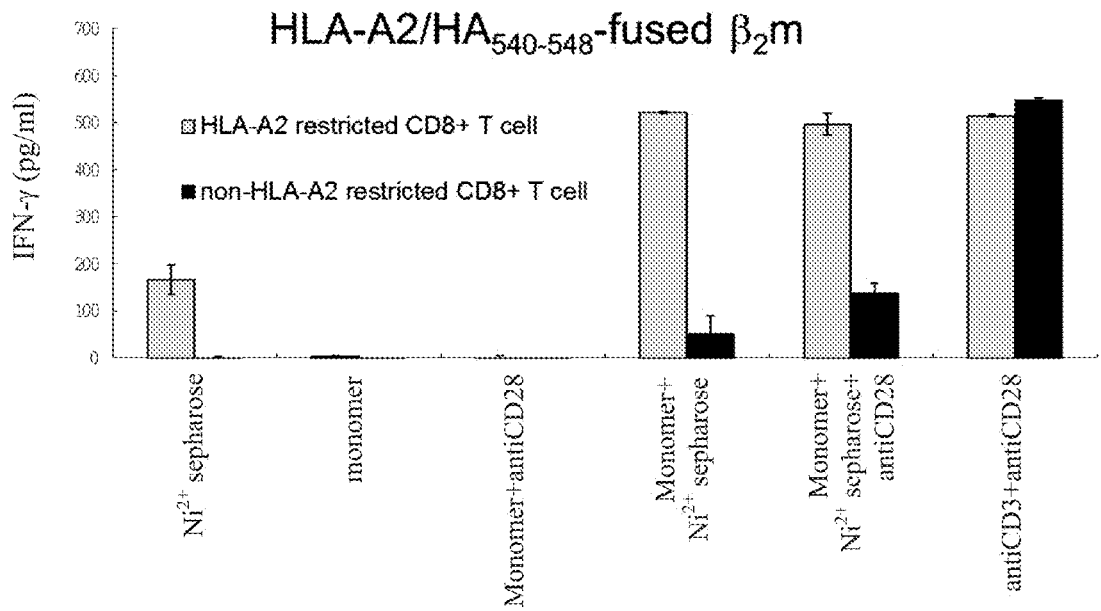
Figure 10:
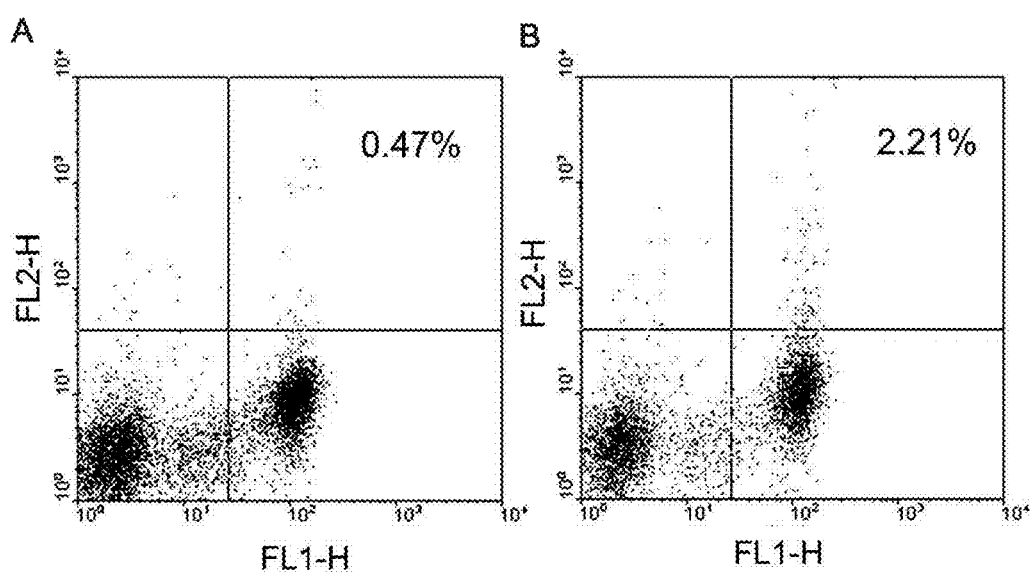
FIG. 10 shows the proliferation of CD8+ T cells stimulated by 2C HLA-A*0201/peptide-fused $\beta_2$m complex-loaded APPs according to one embodiment of the present invention. HLA-A*0201+ CD8+ T cells were co-cultured with (A)

Results:

The IP assay was employed to further confirm the correct conformation of refolded HLA-A*0201/peptide-fused $\beta_2$m and HLA-A*1101/peptide-fused $\beta_2$m complexes. The $\beta_2$m-specific mAb L368 was used to capture complexes. The captured proteins were analyzed by Western blotting with mAb L368 and the HLA class I heavy chain-specific mAb TP25.99. As shown in FIG. 7, the heavy chain and $\beta_2$m were detected in all of the mAb L368-captured refolded complexes. These results suggested that the HLA class I heavy chains were associated with $\beta_2$m in the process of refolding. Combining the results of FIGS. 5, 6 and 7, it was concluded that in vitro refolding of the 2C MHC class I complex was efficient and correct.

Example 6

Analysis of the Function of Refolded HLA-A*0201/Peptide Fused $\beta_2$m Complexes by Detecting IFN-$\gamma$ Secretion from HLA-matched Lymphocytes Co-cultured with HLA-A*0201/M1$_{58-66}$-fused $\beta_2$m-loaded APPs.
Methods:
1. Isolation of Lymphocytes from Human Whole Blood Ficoll-Paque PLUS (GE Healthcare Biosciences) is a sterile density gradient medium containing polymer of sucrose and epichlorohydrin, sodium diatrizoate and calcium disodium ethylenediamintetraacetic acid (EDTA) for isolating lymphocytes from whole blood and is based on the methodology established by Bøyum. Blood was drawn out from healthy donors into a vacuum collection tube coated with heparin (BD Biosciences, San Jose, Calif.). For separating lymphocytes, the anticoagulant-treated blood was diluted with PBS with the ratio of 1:1 and layered carefully over the Ficoll-Paque medium without intermixing in a 50 ml centrifuge tube with the ratio of 2:1. After a short centrifugation for 30 mins at 2500 rpm at room temperature, the lymphocytes and monocytes were harvested from the interface between the layer of Ficoll-Paque and plasma. The plasma was removed and the interphase was transferred carefully into a new 15 ml centrifuge tube. The harvested PBMCs were centrifuged at 1200 rpm for 10 mins in 10 ml PBS to wash the PBMCs and to remove the platelets. The PBMCs were resuspended in RPMI-1460 (HyClone, Thermo Fisher Scientific Inc. Pittsburgh, Pa.) with 10% fetal bovine serum (FBS) and incubated at 37° C. with 5% $CO_2$ for 14 hrs. The suspended cells, peripheral blood lymphocytes (PBLs), were collected for further use.
2. Detection of IFN-$\gamma$ Secretion PBLs were isolated from HLA-A11$^-$, HLA-A2$^-$, HLA-A2$^+$ and HLA-A11$^+$ healthy donors. For stimulating the activity of specific CD8$^+$ T cells, PBLs ($2\times10^5$/100 µl·/test) were cultured under various conditions in triplicate: 1) with 30 µl PBS; 2) with 1 µl·Ni$^{2+}$ SEPHAROSE beads in 30 µl PBS; 3) with 1 µg 2C MHC class I/peptide-fused $\beta_2$m complex monomers in 30 µl PBS; 4) with pre-coated 1 µg anti-CD28 mAb (BioLegend, San Diego, Calif.) and 1 µg 2C MHC class I/peptide-fused $\beta_2$m complex monomers in 30 µl PBS; 5) with 2C MHC class I/peptide-fused $\beta_2$m complex-loaded APPs (1 µg 2C MHC class I/peptide-fused $\beta_2$m complex+1 µl Ni$^{2+}$ SEPHAROSE beads mixed at 4° C. for 14 hrs in 30 µl PBS; 6) with pre-coated 1 µg anti-CD28 mAb and 2C MHC class I/peptide-fused $\beta_2$m complex-loaded APPs; and 7) with pre-coated anti-CD28 and anti-CD3 mAb (BioLegend) as a positive control. Three days later, the PBL-APP mixtures were subjected to centrifugation and the supernatant was collected for analysis of IFN-$\gamma$ secretion by using the human IFN-$\gamma$ ELISA titer kit (eBioscience Inc., San Diego, Calif.). Briefly, 30 µl □ supernatant and 50 µl biotinylated IFN-$\gamma$-specific antibodies were added to each well which had been coated with another IFN-$\gamma$-specific antibody. Each well was then incubated with streptavidin-HRP at room temperature for 30 mins. Next, each well was washed, incubated with the TMB substrate for 30 mins and reaction was measured for the O.D. value at 450 nm. The results of the IFN-$\gamma$ levels were shown in average O.D. value at 450 nm for each control and experimental group.
Results:

Previous data have shown that the 2C MHC class I/peptide-fused $\beta_2$m complexes could be refolded efficiently and correctly in vitro. To enhance the function of refolded 2C complexes, each refolded complex was mixed with Ni$^{2+}$ SEPHAROSE beads to form a giant 2C complex polymer, i.e., APPs. As shown in FIG. 11, the Ni$^{2+}$ SEPHAROSE beads (average 34 µm) is larger than normal T cells (average 5 µm). To analyze whether APPs could stimulate antigen-specific CD8$^+$ T cells, each kind of APPs was co-cultured with PBLs derived from donors expressing matched (test groups) and unmatched (control groups) alleles in vitro. Three days later, the level of IFN-$\gamma$ secretion was measured by using the IFN-$\gamma$-specific ELISA titer kit. IFN-$\gamma$ secretion served as an indicator of T cell activation. As shown in FIG. 12, the APPs were able to stimulate marked HLA class I-restricted T cell response in both HLA-A*0201/M1$_{58-66}$-fused $\beta_2$m-loaded and HLA-A*0201/HA$_{540-548}$-fused $\beta_2$m-loaded conditions (p<0.01). Notably, the APPs loaded with HLA-A*0201/HA$_{540-548}$-fused $\beta_2$m stimulated a prominent T cell response even without the presence of CD28 co-stimulatory signal. Therefore, there was strong evidence for the ability of APPs to stimulate HLA class I-restricted, antigen-specific T cell response.

Example 7

Analysis of the Function of Refolded HLA-A*0201/Peptide-fused $\beta_2$m Complexes by Co-culturing APPs with HLA-matched Lymphocytes to Detect the Proliferation of Antigen-Specific CD8$^+$ T Cells
Methods:
1. Flow Cytometric Analysis PBLs were isolated from HLA-A2$^+$ healthy donors. First, HLA-A2/M1$_{58-66}$-fused $\beta_2$m complexes (5 µg) were mixed with 5 µl of pre-cleaned Ni$^{2+}$-magnetic SEPHAROSE beads at 4° C. for 14 hrs. Then, these beads were co-cultured with previously isolated PBLs ($8\times10^5$ cells/500 µl) in 24-well plates and incubated at 37° C. with 5% $CO_2$ for 5 days. PBLs co-cultured with unloaded SEPHAROSE beads served as the control. After 5 days of incubation, loaded and unloaded SEPHAROSE beads were removed by magnetic drill and PBLs were isolated. These PBLs were then labeled with 2C HLA-A2/M1$_{58-66}$-fused $\beta_2$m complex tetramer made by connecting HLA-A2/M1$_{58-66}$-fused $\beta_2$m complex monomer with anti-His$_6$ mouse mAb (BioVision, Mountain View, Calif.) and R-phycoerythrin (R-PE)-conjugated F(ab')$_2$ fragments of goat anti-mouse Fc antibodies (1:200) (Jackson ImmunoResearch Laboratories) for 1 hr in the dark and washed three times with 1% BSA/PBS. Subsequently, the tetramer-labeled PBLs were labeled with FITC-conjugated anti-CD8 mAb (0.2 µl for each test) (BD Bioscience) for 30 mins in the dark, washed three times with 1% BSA/PBS and resuspended in PBS. After fixation with 0.5% paraformaldehyde/PBS at room temperature for 20 mins, cells were analyzed by FACSCalibur (BD Bioscience) with the Cellquest software (BD Bioscience). Results were expressed as dot plots to compare the frequencies of double-positive populations between the test and control groups.
Results:

As shown in FIG. 13, the frequency of double-positive cells in PBLs co-cultured with HLA-A*0201/M1$_{58-66}$-fused $\beta_2$m-loaded SEPHAROSE beads increased approximately 5 folds compared with that of the PBLs co-cultured with unloaded Ni$^{2+}$ SEPHAROSE beads. Therefore, the APPs could induce the proliferation of antigen-specific CD8$^+$ T cells.

One skilled in the art readily appreciates that the present invention is well adapted to carry out the objects and obtain the ends and advantages mentioned, as well as those inherent therein. The animals, processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. An antigen presenting composition comprising a plurality of 2-component MHC class I complexes and a carrier,
wherein the 2-component MHC class I complex comprises an α heavy chain attached to the carrier and a peptide-fused $β_2$m subunit,
wherein the peptide-fused $β_2$m subunit comprises a peptide capable of binding to class I MHC and a $β_2$m subunit; wherein the peptide is connected to the N-terminus of the $β_2$m subunit with a linker,
wherein the linker consists of the amino acid sequence of SEQ ID NO:15.

2. The composition of claim 1, wherein the α heavy chain is $His_6$-tagged at the C-terminus when the carrier is nickel ion-modified.

3. The composition of claim 2, wherein the carrier is made of $Ni^{2+}$ crosslinked agarose resin beads or $Ni^{2+}$ magnetic beads.

4. The composition of claim 1, wherein the peptide is derived from an antigen.

5. The composition of claim 1, which further comprises a costimulatory molecule.

6. The composition of claim 5, wherein the co-stimulatory molecule comprises recombinant B7, an integrin or and ICAM-1.

7. A method for activating a group of antigen-specific $CD8^+$ T cells in vitro comprising incubating a group of naïve $CD8^+$ T cells with the composition of claim 1.

8. The method of claim 7, wherein the peptide-fused β2m subunit of said composition comprises a peptide that is derived from an antigen that the antigen-specific $CD8^+$ T cells are against.

9. A method for inducing the proliferation of a group of antigen-specific $CD8^+$ T cells comprising incubation of a group of naïve $CD8^+$ T cells with the composition of claim 1.

10. The method of claim 9, wherein the peptide-fused β2m subunit of said composition comprises a peptide that is derived from an antigen that the antigen-specific $CD8^+$ T cells are against.

* * * * *